US006923979B2

(12) United States Patent
Fotland et al.

(10) Patent No.: US 6,923,979 B2
(45) Date of Patent: Aug. 2, 2005

(54) METHOD FOR DEPOSITING PARTICLES ONTO A SUBSTRATE USING AN ALTERNATING ELECTRIC FIELD

(75) Inventors: Richard Fotland, Holliston, MA (US); John Bowers, Clarksburg, NJ (US); William Jameson, West Windsor, NJ (US)

(73) Assignee: Microdose Technologies, Inc., Monmouth Junction, NJ (US)

( * ) Notice: Subject to any disclaimer, the term of this patent is extended or adjusted under 35 U.S.C. 154(b) by 0 days.

(21) Appl. No.: 09/299,388

(22) Filed: Apr. 27, 1999

(65) Prior Publication Data

US 2002/0085977 A1 Jul. 4, 2002

(51) Int. Cl.[7] .......................... A61K 47/00; A61K 9/00; B05B 5/00; B05D 1/04

(52) U.S. Cl. ....................... 424/439; 424/463; 424/474; 424/489; 424/490; 427/457; 427/458; 427/472; 427/475; 427/483

(58) Field of Search ............................ 424/45, 46, 489, 424/457, 458, 472, 475, 483, 439, 463, 474, 490; 427/458, 472, 475, 483, 457

(56) References Cited

U.S. PATENT DOCUMENTS

| | | | | |
|---|---|---|---|---|
| 1,121,452 A | 12/1914 | Bagnall | |
| 3,241,625 A | 3/1966 | Soojian | 177/120 |
| 3,437,074 A | 4/1969 | Hagopain et al. | 118/623 |
| 3,831,606 A | 8/1974 | Damani | 128/266 |
| 3,889,636 A | 6/1975 | Smith | 118/621 |
| 3,943,437 A | 3/1976 | Mourier | 324/32 |
| 3,971,377 A | 7/1976 | Damani | 128/266 |
| 3,977,323 A | 8/1976 | Pressman et al. | 101/426 |
| 3,981,695 A | 9/1976 | Fuchs | 55/138 |
| 3,999,119 A | 12/1976 | Bares | 324/32 |
| 4,021,587 A | 5/1977 | Banker | 427/18 |
| 4,047,525 A | 9/1977 | Kulessa et al. | 128/208 |
| 4,071,169 A | 1/1978 | Dunn | 222/76 |
| 4,072,129 A | 2/1978 | Bright et al. | 118/629 |
| 4,088,093 A | 5/1978 | Pan | 118/630 |
| 4,160,257 A | 7/1979 | Carrish | 346/159 |
| 4,170,287 A | 10/1979 | Edwards et al. | 198/657 |
| 4,197,289 A | 4/1980 | Sturzenegger et al. | 424/21 |
| 4,204,766 A | 5/1980 | Harada | 356/404 |
| RE30,401 E | 9/1980 | White | 204/192 |
| 4,252,434 A | 2/1981 | Nakamura et al. | 355/15 |
| 4,255,777 A | 3/1981 | Kelly | 361/228 |
| 4,324,812 A | 4/1982 | Bentley | 427/8 |
| 4,332,789 A | 6/1982 | Mlodozeniec | 424/27 |
| 4,349,531 A | 9/1982 | Mlodozeniec et al. | 424/27 |
| 4,379,969 A | 4/1983 | Cobb et al. | 250/324 |
| 4,399,699 A | 8/1983 | Fujishiro | 73/304 |
| 4,502,094 A | 2/1985 | Lewin et al. | 361/234 |
| 4,514,781 A | 4/1985 | Plasschaert et al. | 361/230 |
| 4,533,368 A * | 8/1985 | Snaddon et al. | 96/26 |
| 4,538,163 A | 8/1985 | Sheridon | 346/155 |
| 4,554,611 A | 11/1985 | Lewin | 361/234 |
| 4,555,174 A | 11/1985 | Kramer | 355/3 DD |
| 4,561,688 A | 12/1985 | Tsutsui | 294/64.1 |
| 4,570,630 A | 2/1986 | Elliott et al. | 128/203.15 |
| 4,594,901 A | 6/1986 | Norman | 73/861.04 |
| 4,626,876 A | 12/1986 | Miyagawa et al. | 346/160 |
| 4,627,432 A | 12/1986 | Newell et al. | 128/203.15 |
| 4,628,227 A | 12/1986 | Briere | 315/111.81 |
| 4,652,318 A | 3/1987 | Masuda et al. | 156/89 |

(Continued)

FOREIGN PATENT DOCUMENTS

| | | | |
|---|---|---|---|
| EP | 0431924 | 1/1996 | B29C/67/24 |
| EP | 0 885 662 | 12/1998 | B05D/1/06 |
| EP | 0 891 817 | 1/1999 | B05B/5/08 |
| GB | 2 253 164 | 9/1992 | |
| JP | 57-196211 | 12/1982 | |
| JP | 59-150760 | 8/1984 | |
| JP | 4277126 | 10/1992 | 198/690.01 |
| WO | 93/09832 | 5/1993 | |
| WO | 94/08552 | 4/1994 | |
| WO | 94/13271 | 6/1994 | |
| WO | 94/23772 | 10/1994 | |
| WO | 95/00127 | 1/1995 | |
| WO | 9800337 | 1/1998 | B65B/1/30 |
| WO | 98/42446 | 10/1998 | B05B/5/025 |
| WO | 98/52206 | 11/1998 | |

OTHER PUBLICATIONS

The Columbia Encyclopedia, Fifth Ed. (1994), "gas" (http://www.slider.com/enc/21000/gas.htm).*

Remington's Pharmaceutical Sciences (17th Ed. 1985), p. 281.*

Merriam–Webster's Collegiate Dictionary (10th Ed. 1998), p. 1293.*

Science News, vol. 151, p. 205, "Ink jets not just for the printed page". (Apr. 5, 1997).

Journal of Imaging Technology, vol. 12. No. 3, pp. 144–151 "Ion Printing Technology," By John R. Rumsey and David Bennewitz, June 1966.

Focal Press—London, Focal/Hastings House—New York, "Electrophotography," By R.M. Schaffert, 1975, pp. 41–42, 51, 72–74, 195, 196.

(Continued)

*Primary Examiner*—S. Mark Clardy
*Assistant Examiner*—Frank Choi
(74) *Attorney, Agent, or Firm*—Hayes Soloway P.C.

(57) ABSTRACT

Uniform portions of fine powders are deposited on a substrate by electrostatic attraction in which the charge of the electric field and polarity of the charged particles are varied repeatedly to form a buildup of powder on the carrier surface.

47 Claims, 4 Drawing Sheets

U.S. PATENT DOCUMENTS

| | | | | |
|---|---|---|---|---|
| 4,664,107 | A | 5/1987 | Wass | 128/200.23 |
| 4,685,620 | A | 8/1987 | Law et al. | 239/3 |
| 4,734,722 | A | 3/1988 | Maczuszenko et al. | 346/159 |
| 4,779,564 | A | 10/1988 | Kiefer et al. | 118/624 |
| 4,811,731 | A | 3/1989 | Newell et al. | 128/203.15 |
| 4,848,267 | A | 7/1989 | Slayton et al. | 118/653 |
| 4,860,417 | A | 8/1989 | Tajima et al. | 29/130 |
| 4,875,060 | A | 10/1989 | Masuda et al. | 346/155 |
| 4,878,454 | A | 11/1989 | Cann | 118/663 |
| 4,889,114 | A | 12/1989 | Kladders | 128/203.15 |
| 4,917,978 | A | 4/1990 | Ritt et al. | 430/23 |
| 4,918,468 | A | 4/1990 | Miekka et al. | 346/159 |
| 4,921,727 | A | 5/1990 | Datta et al. | 427/57 |
| 4,921,767 | A | 5/1990 | Datta et al. | 430/23 |
| 4,948,497 | A | 8/1990 | Ohkawa | 209/1 |
| 4,971,257 | A | 11/1990 | Birge | 239/708 |
| 4,992,807 | A | 2/1991 | Thomson | 346/155 |
| 5,005,516 | A | 4/1991 | Speer | 118/657 |
| 5,014,076 | A | 5/1991 | Caley, Jr. et al. | 346/159 |
| 5,027,136 | A | 6/1991 | Fotland et al. | 346/159 |
| 5,028,501 | A | 7/1991 | Ritt et al. | 430/23 |
| 5,031,610 | A | 7/1991 | Armstrong et al. | 128/200.23 |
| 5,080,380 | A | 1/1992 | Nakagawa et al. | 279/1 |
| 5,102,045 | A | 4/1992 | Diana | 239/3 |
| 5,102,690 | A | 4/1992 | Iyer et al. | 427/57 |
| 5,115,803 | A | 5/1992 | Sioutas | 128/200 |
| 5,126,165 | A | 6/1992 | Akihama et al. | 427/531 |
| 5,161,524 | A | 11/1992 | Evans | 128/203.15 |
| 5,176,132 | A | 1/1993 | Drought et al. | 128/203.15 |
| 5,186,164 | A | 2/1993 | Raghuprasad | 128/200.14 |
| 5,204,055 | A | 4/1993 | Sachs et al. | 419/2 |
| 5,214,386 | A | 5/1993 | Singer et al. | 324/452 |
| 5,239,993 | A | 8/1993 | Evans | 128/203.15 |
| 5,243,970 | A | 9/1993 | Ambrosio et al. | 128/203.15 |
| 5,263,475 | A | 11/1993 | Altermatt et al. | 128/203.15 |
| 5,278,588 | A | 1/1994 | Kubelik | 346/159 |
| 5,301,666 | A | 4/1994 | Lerk et al. | 128/203.15 |
| 5,310,582 | A | 5/1994 | Vyakarnam et al. | 427/560 |
| 5,327,883 | A | 7/1994 | Williams et al. | 128/203.12 |
| 5,328,539 | A | 7/1994 | Sato | 156/275.5 |
| 5,377,071 | A | 12/1994 | Moslehi | 361/234 |
| 5,404,871 | A | 4/1995 | Goodman et al. | 128/200.14 |
| 5,421,816 | A | 6/1995 | Lipkovker | 604/20 |
| 5,454,271 | A | 10/1995 | Yamamoto et al. | 73/861.04 |
| 5,463,525 | A | 10/1995 | Barnes et al. | 361/234 |
| 5,490,962 | A | 2/1996 | Cima et al. | 264/22 |
| 5,522,131 | A | 6/1996 | Steger | 29/829 |
| 5,534,309 | A | 7/1996 | Liu | 427/458 |
| 5,655,523 | A | 8/1997 | Hodson et al. | 128/315 |
| 5,669,973 | A | 9/1997 | Pletcher | 118/624 |
| 5,699,649 | A | 12/1997 | Abrams et al. | 53/428 |
| 5,714,007 | A | 2/1998 | Pletcher et al. | 118/629 |
| 5,846,595 | A | 12/1998 | Sun et al. | 427/2.14 |
| 5,858,099 | A | 1/1999 | Sun et al. | 118/621 |
| 6,007,630 | A | 12/1999 | Pletcher et al. | 118/624 |
| 6,028,615 | A | 2/2000 | Pletcher et al. | 347/127 |
| 6,032,871 | A | 3/2000 | Borner et al. | 239/3 |
| 6,063,194 | A | 5/2000 | Poliniak et al. | 118/623 |
| 6,074,688 | A | 6/2000 | Pletcher et al. | 427/2.14 |
| 6,096,368 | A | 8/2000 | Sun | 427/2.14 |
| 6,146,685 | A | 11/2000 | Chrai et al. | 427/2.14 |
| 6,149,774 | A | 11/2000 | Sun et al. | 204/164 |

OTHER PUBLICATIONS

Van Nostrand Reinhold—New York, "Imaging Processes and Materials" Neblette's Eighth Edition, Edited by John Sturge , Vivian Walworth & Allan Shepp, pp. 164.

"The Science of Power Coatings" vol. 2, 1994, Applications, By David A. Bate, J. Copland, R. Floyd, M. Letts, Eur. Ing. Dr. J.A. Scott Ph.D., E. Tweddle BSc DMS; pp. 69–71.

Petition and Amendment under 37 CFR 1.48(a) dated dated Sep. 13, 1996. In re application of: Hoi Cheong Steve Sun et al. U.S. Appl. No. 08/630,050,titled: Electrostatic Chucks filed Apr. 9, 1996.

Declaration and Powers of Attorney, U.S. Appl. No. 08/630, 050 "Electrostatic Chucks," DSRC 11918.

In re: U.S. Appl. No. 08/630,050 the following: (1) Figs. 1–27; (2) Notice to File Missing Parts of Application, dated May 23, 1996; Declaration & Powers of Attorney executed in Jun., 1996; Filing of Missing Parts of Application dated Jun. 20, 1995; and Information Disclosure Statement Under 37 CFR 1.56 dated Jul. 9, 1996.

* cited by examiner

METHOD FOR DEPOSITING PARTICLES ONTO A SUBSTRATE USING AN ALTERNATING ELECTRIC FIELD

BACKGROUND OF THE INVENTION

This invention is directed towards the deposition of small (usually fractional gram) masses on a generally electrically non-conductive substrate. One of the most common methods for accomplishing the goal is practiced by manufacturers of photocopiers and electrophotographic electronic printers. This involves causing charged toner particles to migrate with an electric field to a charged area on a photoreceptor, so-called electrostatic deposition. While electrostatic deposition has been proposed for packaging powdered drugs (see U.S. Pat. Nos. 5,669,973 and 5,714,007 to Pletcher), electrostatic deposition is limited by the amount of mass that can be deposited in a given area.

This limitation is intrinsic to electrostatic deposition technology and is determined by the combination of the amount of charge that can be placed on the photoreceptor and the charge to mass ratio of the toner particles. The mass that can be deposited in an area of a substrate is limited to the charge in the area divided by the charge to mass ratio of the particles being deposited. The maximum amount of charge that can be deposited in an area of a substrate is determined by the substrate electrical properties, the electrical and breakdown properties of the air or gas over it, and by the properties of mechanism used for charging the substrate. Likewise, the minimum charge to mass ratio of particles (which determines the maximum mass that can be deposited) is determined by the charging mechanism. However, as the charge to mass ratio is decreased, the variation in the charge to mass ratio increases even to the point where some particles may be oppositely charged relative to the desired charge on the particles. This variation prevents the reliable deposition of a controlled mass on the substrate. Furthermore, low charge to mass ratio particles limit the overall speed of deposition because the force of a particle, which sets the particle velocity, from an electrostatic field is proportional to the charge carried by the particle. For these reasons, higher charge to mass ratio particles are generally preferred.

Packaged pharmaceutical doses, in the range of 15 to 6000 $\mu$g are employed in dry powder inhalers for pulmonary drug delivery. A mean particle diameter of between 0.5 and 6.0 $\mu$m is necessary to provide effective deposition within the lung. It is important that the dose be metered to an accuracy of +/−5%. A production volume of several hundred thousand per hour is required to minimize production costs. High speed weighing machines are generally limited to dose sizes over about 5,000 $\mu$g and thus require the active pharmaceutical be diluted with an excipient, such as lactose powder, to increase the total measured mass. This approach is subject to limitations in mixing uniformity and the aspiration of extraneous matter. Hence, electrostatic deposition of such pharmaceutical powders is highly desirable.

U.S. Pat. No. 3,997,323, issued to Pressman et al, describes an apparatus for electrostatic printing comprising a corona and electrode ion source, an aerosolized liquid ink particles that are charged by the ions from the ion source, a multi-layered aperture interposed between the ion source and the aerosolized ink for modulating the flow of ions (and hence the charge of the ink particles) according to the pattern to be printed. The charged ink particles are accelerated in the direction of the print receiving medium. This patent discusses the advantages in the usage of liquid ink particles as opposed to dry powder particles in the aerosol. However, from this discussion it is apparent, aside from the disadvantages, that dry powder particles may also be used. Furthermore, the charge to mass ratios achieved from using an ion source for charging the powder particles are much higher than those generally achieved using triboelectric charging (commonly used in photocopies and detailed by Pletcher et al in U.S. Pat. No. 5,714,007), thereby overcoming the speed issue discussed above. Such printers have been commercially marketed and sold. However, an apparatus for depositing powder on a dielectric (i.e. a powder carrying package) using the Pressman approach also suffers from the above described maximum amount of powder that can be deposited on the dielectric. This is because during the deposition process, charge from both the ions and the charged particles accumulates on the dielectric, ultimately resulting in an electric field that prevents any further deposition. In other words, the amount of material that can be deposited on the dielectric packaging material is limited by the amount of charge that can be displaced across it which is determined by the capacitance of the dielectric and the maximum voltage that can be developed across it.

SUMMARY OF THE INVENTION

The above disadvantages are overcome in the present invention by providing an alternating electric field for depositing particles onto a dielectric substrate. More particularly, the present invention comprises a method and apparatus for depositing particles from an aerosol onto a dielectric substrate wherein the method comprises and the apparatus embodies the following steps: charging the aerosol particles, positioning them in a deposition zone proximate to the dielectric, and applying an alternating field to the deposition zone by which the aerosol particles are removed from the aerosol and deposited on the dielectric substrate thus forming a deposit. The alternating field provides the means to deposit charged particles and/or ions such that the accumulation of charge on the dielectric substrate does not prevent further deposition of particles thus enabling electrostatic deposition of a deposit with relatively high mass.

In one embodiment of the invention, the particles are alternately charged in opposite polarities and deposited on the substrate with the alternating electric field, thus preventing charge accumulation on the dielectric substrate.

In a second embodiment, an ion source is provided in the deposition zone to provide ions of both polarities for charging the particles. The alternating field determines which polarity of ions is extracted from the ion source. These extracted ions may be used for charging the particles and/or discharging the deposited particles on the dielectric substrate.

In a third embodiment substantially all of the particles are removed from the aerosol. In this embodiment, the mass of the deposit is controlled by measuring the mass flow into the deposition zone and controlling the deposition time to accumulate the desired mass of deposit.

In yet another embodiment, the mass of the deposit is determined by measuring the mass flow both into the deposition zone and immediately downstream thereof, and the difference being the amount deposited.

BRIEF DESCRIPTION OF THE DRAWINGS

The foregoing and other advantages of the present invention will become apparent from the following description taken together with the accompanying drawings in which.

DETAILED DESCRIPTION

Figure 1:
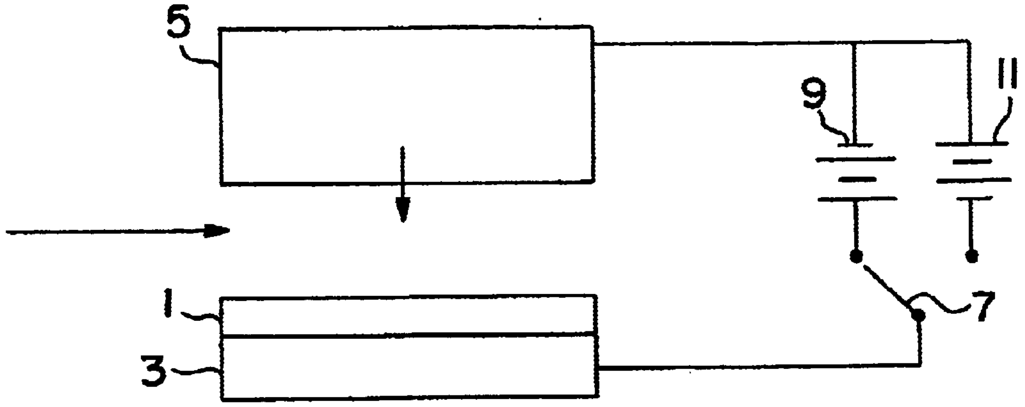
FIG. 1 depicts a schematic cross section of a deposition apparatus made in accordance with the present invention.
Figure 2:
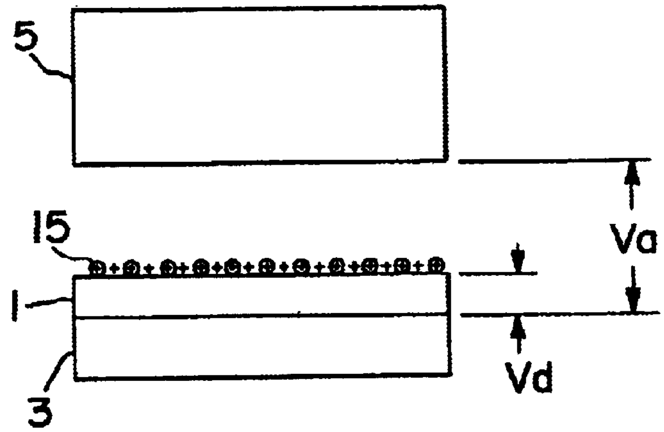
FIG. 2 illustrates voltage differences in the deposition apparatus of FIG. 1.
Figure 3:
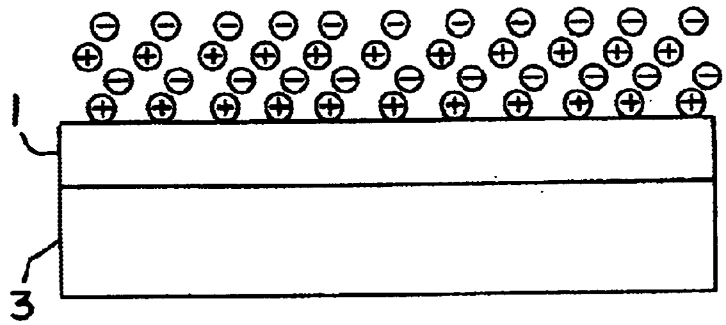
FIG. 3 depicts an article made in accordance with the present invention.

The present invention provides a method and apparatus for depositing a relatively large mass of material upon a dielectric substrate and the resulting deposition product. The general apparatus for carrying out this deposition is shown in FIG. 1 and includes a first electrode 5, a dielectric substrate 1 closely proximate to or in contact with a second electrode 3, also herein referred to as a deposition electrode. The volume between the dielectric substrate 1 and the first electrode 5 comprises a deposition zone into which aerosol particles are introduced. This is indicated by the horizontal arrow of FIG. 1. An alternating electric field (the deposition field), indicated by the vertical arrow in FIG. 1 is created within the deposition zone by first electrode 5, second electrode 3 in combination with an alternating voltage source, shown in FIG. 1 as comprising batteries 9 and 11 and switch 7 wherein the polarity of the field generating voltage is determined by the position of switch 7. However, any suitable means for generating an alternating voltage is contemplated to be within the scope of the invention. Charged particles from the aerosol within the deposition zone are electrostatically attracted to the substrate 1 thereby forming a deposit 15 as shown in FIG. 2. The deposit is incrementally formed from groups of particles deposited from each cycle of the alternating field thereby forming a deposit with a relatively larger mass than is possible if a static electric field were to be used. The process of forming the deposit may be terminated by removal of the alternating field. The completed deposit is shown in FIG. 3 as deposited on the dielectric substrate 1.

The aerosol particles may comprise a dry powder or droplets of a liquid. In one particular embodiment of this invention, the particles comprise a pharmaceutical, for example, albuterol. The pharmaceutical deposits made from deposited pharmaceutical particles may, for example, form a dosage used in a dry powder inhaler. In a second embodiment of this invention, the particles comprise a carrier coated with a biologically active agent. An example of a bioactive agent coated carrier is a gold particle (the carrier) coated by fragments of DNA (the bioactive agent). Such particles are used for gene therapy. The prior examples are intended to exemplify the applications of the invention, and not intended to limit the scope of it.

The aerosol gas may comprise air or any other suitable gas or gas mixture. For some applications where it is desired to control precisely the environment to which the particles are exposed, and/or to control ion emission characteristics (discussed subsequently), pure nitrogen, or nearly pure nitrogen mixed with a small percentage of another gas, e.g. carbon dioxide, is preferred.

Basic components of an aerosol generator include means for continuously metering particles, and means for dispersing the particles to form an aerosol. A number of aerosol generators have been described in the literature and are commercially available. The most common method of dispersing a dry powder to form an aerosol is to feed the powder into a high velocity air stream. Shear forces then break up agglomerated particles. One common powder feed method employs a suction force generated when an air stream is expanded through a venturi to lift particles from a slowly moving substrate. Powder particles are then deagglomerated by the strong shear force encountered as they pass through the venturi. Other methods include fluidized beds containing relatively large balls together with a chain powder feed to the bed, sucking powder from interstices into a metering gear feed, using a metering blade to scrape compacted powder into a high velocity air stream, and feeding compacted powder into a rotating brush that carries powder into a high velocity air stream. A Krypton 85 radioactive source may be introduced into the aerosol stream to equilibrate any residual charge on the powder. Alpha particles from the source provide a bipolar source of ions that are attracted to charged powder resulting in the formation of a weakly charged bipolar powder cloud.

Non-invasive aerosol concentration (and mass density for aerosols of known particle size and specific density) may be determined optically by using right angle scattering, optical absorption, phase-doppler anemometry, or near forward scattering. A few commercially available instruments permit the simultaneous determination of both concentration and particle size distribution.

Particles may be charged within or outside of the deposition zone. One contemplated method of charging particles is triboelectric charging. Triboelectric charging occurs when the particles are made to come in contact with dissimilar materials and may be used with the particles are from a dry powder. Triboelectric charging is well known and widely used as a means to charge toner particles in photocopying and electrophotographic electronic printing processes. Generally, triboelectric charging of particles takes place outside of the deposition zone. A parameter that characterizes the efficacy of particle charging is the charge-to-mass ratio of particles. This parameter is important as it determines the amount of force that can be applied to the particle from an electric field, and therefore, the maximum velocity that particles can achieve during deposition. This, in turn, sets an upper bound to the deposition rate that can be achieved. Charge-to-mass ratios of 1 $\mu$C to 50 $\mu$C per gram are achievable when triboelectrically charging 1 $\mu$m to 10 $\mu$m diameter particles. Such charge-to-mass ratios are documented for pharmaceuticals by Pletcher et al in U.S. Pat. No. 5,714,007. However, other particle charging methods may achieve charge-to-mass ratios at least ten times greater than is possible with triboelectric charging. Accordingly, it is preferred to use such a method to maximize the velocity of the particles when under influence of the deposition field and the rate at which it is possible to form the deposit.

Figure 5:
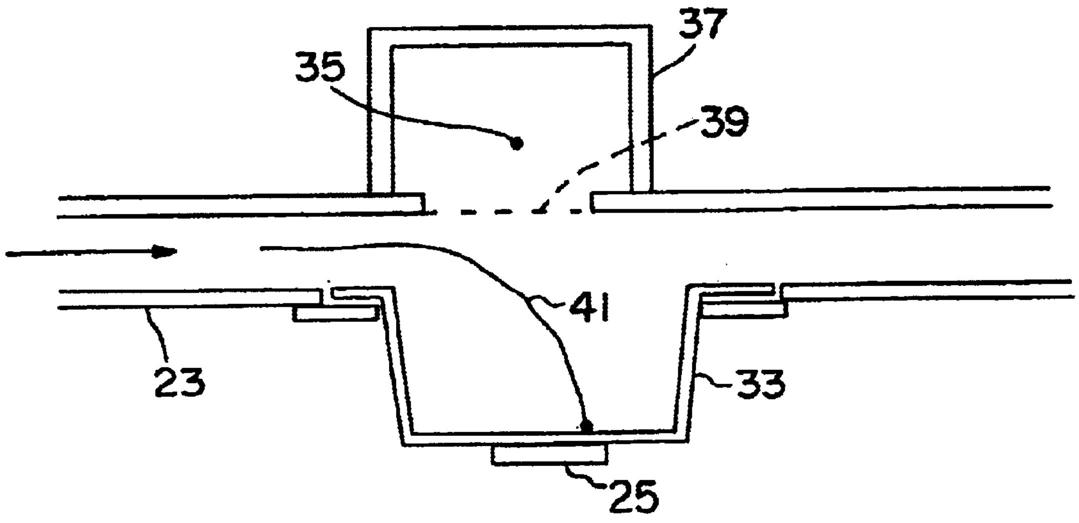
Figure 6:
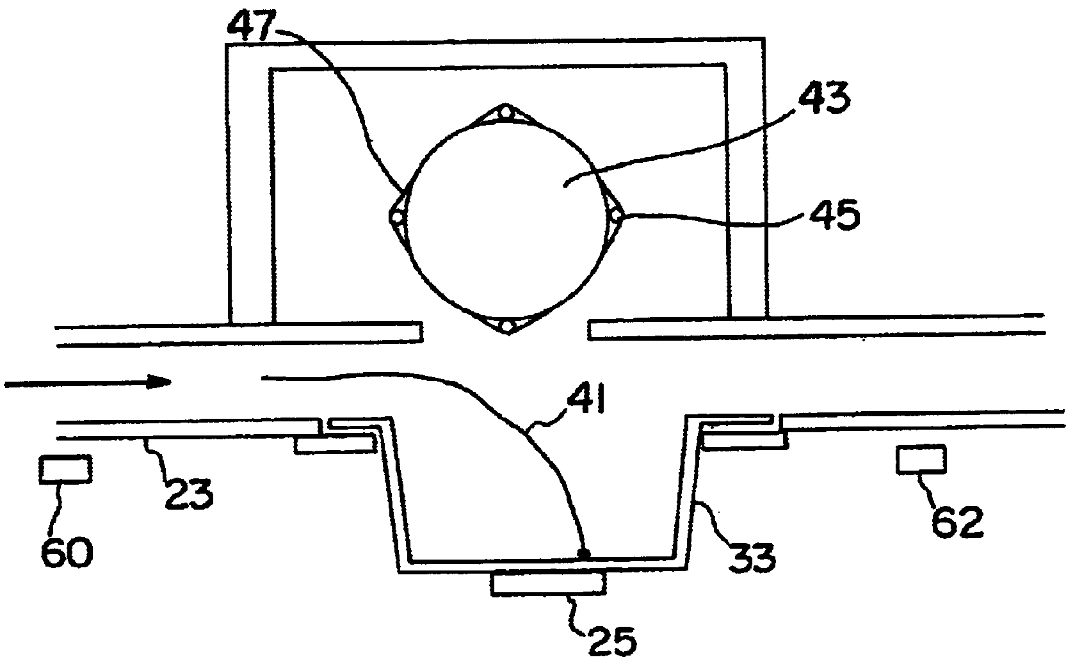

Generally these methods for applying higher amounts of charge to the particles utilize an ion source to generate an abundance of ions of both or either positive and negative polarities. Some of the negative polarity ions may be electrons. As particles from the aerosol pass in front of the ion source (the charging zone), ions of one polarity are accelerated away from the ion source by an electric field through which the particles travel. Ions that impact the particles attach to the particles. Ions continue to impact the particles until the local electric fields from the ions attached to the particles generate a local electric field of sufficient magnitude to repel the oncoming ions. FIGS. 5 and 6 illustrate two approaches for generating charging ions as well as the means for providing an accelerating field.

In FIG. 5 ions are generated using corona wire 35. Ions are accelerated through an open mesh screen 39 from an electric field created between open mesh screen 39 and electrode 25. Housing 37 may be slightly pressurized to prevent the migration of aerosol particles into the corona cavity. Alternatively, the corona source may consist of one or more corona points at the location of corona wire 35. Aerosol enters the charging zone through channel 23. Particles are charged by corona generated ions that pass through the apertures of screen 39. Such a particle charging method is known. A derivative of this method is described by Pressman et al in U.S. Pat. No. 3,977,323. As shown in FIG. 5, electrode 25 is the previously described deposition electrode and open mesh screen is the first electrode of the previously described deposition zone. Likewise, substrate 33 is the previously described dielectric substrate. Thus, in this exemplary configuration, the charging zone and deposition zone are the same and the particles are simultaneously charged and made to deposit. A particle trajectory is shown by path 41.

Figure 7:
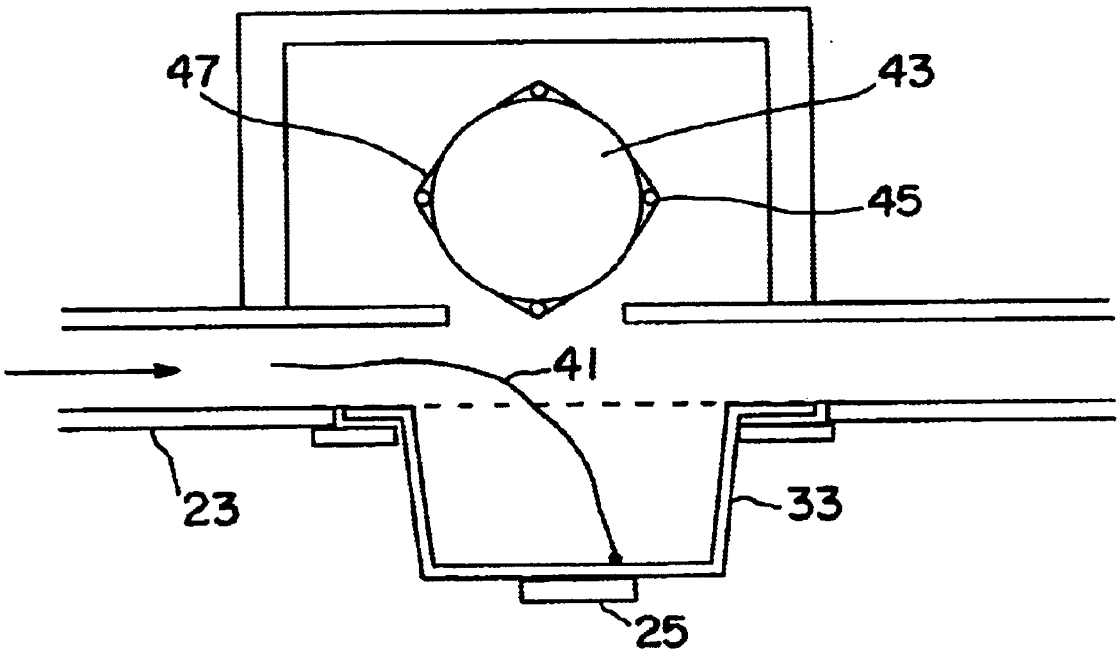

An alternate particle charging method using an ion source employs a silent electric discharge (SED) charge generator. The construction and operation of this class of device is described by D. Landheer and E. B. Devitts, Photographic Science and Engineering, 27, No. 5, 189–192, September/October, 1993 and also in U.S. Pat. Nos. 4,379,969, 4,514,781, 4,734,722, 4,626,876 and 4,875,060. In the exemplary implementation illustrated in FIG. 6, a cylindrical glass core 43 supports four glass coated tungsten wires 45 equally spaced about its surface. The assembly is closely wound with a fine wire 47 in the form of a spiral. A typical generator unit, available from Delphax Systems, Canton, Mass., consists of a 1 cm diameter Pyrex glass rod supporting four glass clad 0.018 cm diameter tungsten wires. The assembly is spiral wound with 0.005 cm diameter tungsten wire at a pitch of about 40 turns per cm. Only one glass coated tungsten wire is activated at any time. The other three wires are spares that may be rotated into the active position if the original active wire becomes contaminated. In FIG. 6, the active wire is that wire closest to the opening in channel 23. Ions and electrons are generated in the region adjacent the glass coated wire when a potential of about 2300VACpp at a frequency of about 120 KHz is applied between the tungsten wire core and the spiral wound tungsten wire. Ions and electrons are withdrawn from the active region by an electric field created between spiral winding 47 and electrode 25. As in FIG. 5, in the exemplary configuration of FIGS. 6 and 7, the aerosol particles are simultaneously charged and made to deposit.

Other ion sources exist that may be suitable for charging particles. For example, it is possible to generate ions with X-rays or other ionizing radiation (e.g. from a radioactive source). When particles are charged with an ion source, any means for making available ions of both or either positive and negative polarity ions is meant to be within the scope of the invention.

Another means for charging particles particularly applicable to liquid droplets is described by Kelly in U.S. Pat. No. 4,255,777. In this approach, charged droplets are formed by an electrostatic atomizing device. Although, the charge-to-mass ratio of such particles cited by Kelly is not as high as can be achieved when charging particles with an ion source, it is comparable to that achievable by triboelectric charging and may be both preferable in some applications of the invention and is, in any case, suitable for use with the present invention.

The above cited configurations are not meant to imply any limitations in configuration. Rather they are meant to serve as examples of possible configurations contemplated by the invention. Therefore, for example, although particle charging with ion sources is shown and discussed wherein particles are charged within the deposition zone, charging of particles with ion sources outside of the deposition zone is also contemplated. All possible combinations of system configuration made possible by the present disclosure are contemplated to be within the scope of the invention.

The alternating deposition field preferably has a frequency between 1 Hz and 10 KHz, and most preferably, frequency between 10 Hz and 1000 Hz, and a magnitude of between 1 KV/cm and 10 KV/cm. Other frequencies and magnitudes are possible, depending upon the system configuration. For example, a higher deposition field magnitude is possible, generally up to 30 KV/cm—the breakdown potential of air and other gases, but not preferred because it may lead to unexpected sparking. Lower deposition field magnitudes are not preferred because the velocity of the aerosol particles in response to the applied field becomes too low. Likewise, an alternating frequency below 1 Hz generally is not preferred for most applications because it is anticipated that charge buildup on the dielectric substrate may substantially diminish the magnitude of the deposition field over periods of a second or more. However, there may be applications where this is not the case. Frequencies of 10 KHz and higher generally are not preferred because it is believed that the charged particles will not have sufficient time to travel through the deposition zone and form the deposition. However, for systems with very small deposition zones, this may not be a factor.

The waveform of the deposition field preferably is rectangular. However, it has been found that triangular and sinusoidal waveforms also are effective in forming deposits, although generally less so. The waveform has a duty cycle, which is defined in terms of a preferred field direction. The duty cycle is the percentage of time that the deposition field is in the preferred field direction. The preferred field direction either may be positive or negative with respect to the deposition electrode depending upon the characteristics of a particular system configuration. The duty cycle preferably is greater than 50% and most preferably 90%. The preferred field direction is that which maximizes the deposition rate.

As previously described, the deposition field is formed between a first electrode and a second, deposition electrode. The first electrode may or may not be an element of an ion emitter. In some configurations of the invention use of an ion emitter in the deposition zone is advantageous in that it helps to discharge the deposited charged particles thereby preventing the buildup of a field from the deposited charged particles that repels the further deposition of particles from the aerosol. This is particularly advantageous when the duty cycle is greater than 50%. Of course, an ion emitter is required in the deposition zone if the aerosol particles are to be charged within the deposition zone. However, it is also possible to control the charging of the particles, synchronously with or asynchronously to the alternation of the deposition field such that the buildup of a particle repelling field from the deposit is minimized.

The dielectric substrate is closely proximate to and preferably in contact with the deposition electrode. By closely proximate is meant that the separation between the dielectric substrate and the deposition electrode is less than the thickness of the dielectric substrate. In this way, the charged aerosol particles are directed to land on the dielectric substrate in an area determined by the contact or closely proximate area of the deposition electrode. Thus, it is possible to control the location and size of the deposit.

The substrate for the deposit may consist of a dielectric material, such as vinyl film, or an electrically conducting material such as aluminum foil. As previously mentioned, as unipolar charged powder is deposited upon the surface of a dielectric, a large electrical potential is formed which generates an electric field that opposes the deposition field and deposition is thus self-limiting at rather low masses. If unipolar charged powder is deposited on the surface of an electrical conductor, then again a surface potential will be built up but of a lower magnitude than that of a corresponding insulating substrate. The ratio of the surface voltage of a deposit on an insulating layer to that of a deposit on the surface of a conducting layer is roughly equal to ratio of the relative thickness of the dielectric plus the thickness of the deposited powder and the thickness of the deposited powder layer. The use of alternating deposition to form bipolar layers through the use of ac aerosol charging and ac deposition fields allows larger masses to be deposited onto the surfaces of conductors.

The dielectric substrate may be any material and have any structure suitable to its other functions. For example, it may be a packaging medium, such as a tablet, capsule or tubule, or the blister of a plastic or metal foil blister package. The dielectric substrate may also be a pharmaceutical carrier, for example, a pill or capsule. It may be any edible material, including chocolate. Alternatively, it may be simply a carrier of the deposit for carrying it to another location for further processing.

We have found with the present invention that it is possible to deposit substantially all of the aerosol particles that pass through the deposition zone under conditions where the flow rate of the aerosol is below a maximum. This maximum flow rate is determined primarily by the magnitude of the deposition field, the charge-to-mass ratio of the charged particles, and their diameters. The capability to deposit substantially all of the aerosol particles has been demonstrated for relatively large mass deposits, much larger than is possible using prior art systems that electrostatically create deposits. For example, we have deposited several milligrams of lactose power into a blister of a blister pack of 6mm diameter. A particular advantage of the present invention is that there are no limits related to charge-to-mass ratio of the charged particles nor the amount of charge laid down on a substrate as there are with prior art systems. The use of an alternating deposition field enables deposition of charge of either polarity on the combination of substrate and deposit, whether the charge is carried by ions or charged particles. The net deposited charge may be therefore neutralized if necessary. As such, the limits to the mass of the deposit become mechanical in nature rather than electrical.

The ability to deposit substantially all of the aerosol particles that pass through the deposition zone provides a new method for controlling the mass of the deposit. In this method the mass flow of the aerosol particles that pass into and out of the deposition zone is measured over time by means of sensors 60, 62 located upstream and downstream of the deposition zone. The results could be recorded for manufacturing control records and adjustments in flow rate, etc., made as need be to maintain a desired deposition amount. As previously mentioned there are various known means for measuring the velocity of an aerosol. In combination, these means enable the measurement of the mass flow rate. The integration of the mass flow rate over time gives the total mass. Accordingly, the mass of a deposit may be controlled by measuring the mass flow of aerosol particles into the deposition zone and upon reaching a desired deposit mass, removing the presence of the alternating deposition field. In circumstances wherein a portion of the total aerosol is not deposited as it passes through the deposition zone, a second measuring instrument may be positioned immediately after the deposition zone. The difference between the two measurements represents the total mass deposited from the aerosol as it passes the deposition zone. The deposit may be controlled by removing the presence of the alternating deposition field as described previously. Even in cases wherein substantially all of the aerosol particles are deposited in the deposition area, the existence of a second measuring instrument provides confirmation of the actual mass deposited, and is of particular interest in applications where the reliability of the mass deposited is of commercial interest such as pharmaceutical dosages. The mass of deposits formed by the present invention is relatively larger than deposits that can be formed with prior art methods that electrostatically create deposits. On the other hand, they may be much smaller than masses conveniently created using prior art methods that mechanically weigh or otherwise mechanically measure or control the mass. As such, the present invention provides a unique means to address a hitherto unaddressed need.

Figure 4:
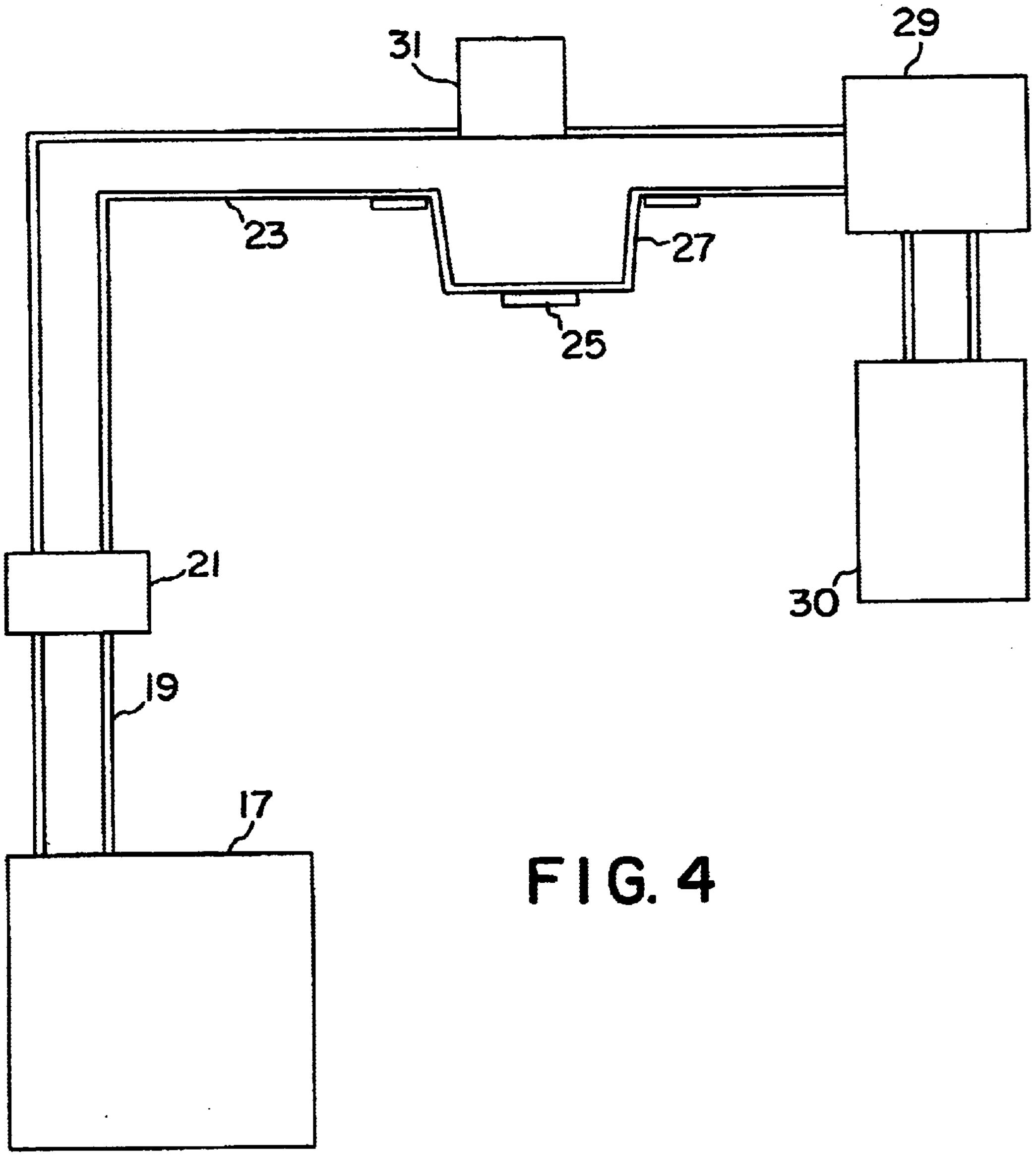
FIGS. 4 to 7 depict schematic views of various preferred embodiments of the present invention.

The details of the invention may be further examined by considering FIG. 4. Here, an aerosol generator 17 forms an air borne particle dispersion that is carried by enclosed channel 19 to aerosol concentration monitoring station 21. Channel 23 then carries the aerosol through a region where charging device 31 charges the powder. An electrostatic field is provided between the charging device 31 and deposition electrode 25. Deposition electrode 25 corresponds to electrode 3 shown in FIG. 1. A dielectric substrate 27 shown here as a blister pack pocket that collects charged particles deflected by the electrostatic field. A second concentration monitoring station 29 is employed to determine how much of the particles have been removed from the aerosol. Under conditions whereby essentially all of the particles are removed from the air stream, this second concentration monitor may not be required. The air stream then moves into collector 30. This collector might consist of a filter or an electrostatic precipitator or both. Alternately, the air may be recirculated through the aerosol generator.

EXAMPLE

A filling device was set up according to the schematic of FIG. 6. The channel was fabricated of ¼-inch thick polycarbonate sheet. The channel width was 40-mm and its height was 6-mm. A blister pack pocket, formed of 6-mil polyvinyl chloride, having a depth of 4-mm and a diameter of 6-mm was supported on a circular electrode 25 having a diameter of 4-mm.

The charge source, consisting of glass core rod 43, spiral wire electrode 47 and four glass coated wire 45 spaced at intervals around the periphery of the core rod, was obtained from Delphax Systems, Canton, Mass. Delphax customers employ these rods in discharging (erasing) latent images on Delphax high-speed printer drums.

Spiral winding 47 was maintained at ground potential and glass coated tungsten wire 45 was excited using 2300 volt peak-to-peak ac at a frequency of 120 kHz. A Trek high voltage amplifier was employed to provide square wave switching of deposition electrode 25 at a frequency of 35 Hertz. The output voltage was switched between +5 kV and −5 kV. The duty cycle was set so that negative charges were extracted for 10% of the square wave period leaving positive charge extraction to occur over 90% of the duty cycle.

An aerosol consisting of lactose powder, having a particle size in the range of about 3 to about 7 microns, was suspended in a flowing stream of nitrogen gas. The lactose was aerosolized by the turbulent action of pressurized nitrogen in a Wright Dust Feed aerosolizer manufactured by BGI Inc., Waltham, Mass. The aerosol concentration was about 1 microgram/cm$^3$ and the channel flow velocity was adjusted to 30 cm/sec.

Charging and deposition potentials were applied for a period of two minutes during aerosol flow. A well-defined mass of powder, measured and found to be 1 mg, was formed at the bottom of the blister pack pocket. No powder deposition was found at the blister pack walls or on the bottom of the channel.

Subsequent experimental runs established that the mass deposited was proportional to the deposition time over the time intervals of ½ to 5 minutes.

With the present invention, it is also possible to multiplex the operation of two or more deposition zones served from a single aerosol source by configuring deposition zones along the aerosol path and selectively applying an alternating deposition field at one deposition zone at a time. Aerosol particles passing into a deposition zone where no alternating deposition field exists simply pass through the deposition zone whereupon they can pass into a next deposition zone.

Although various embodiments which incorporate the teachings of the present invention have been shown and described in detail herein, many other varied embodiments that still incorporate these teachings may be made without departing from the spirit and scope of the present invention. For example, the aerosol particles may comprise carrier particles which may comprise inert substrates including biocompatible metal particles coated with a bioactive agent.

We claim:

1. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby to drive charged particles from the moving gas stream and deposit said charged particles as oppositely charged layers on said dielectric substrate thus forming a built-up deposit; and collecting or recirculating the moving gas stream in a closed system.

2. The method according to claim 1, wherein said aerosol particles comprise liquid droplets charged by a charge injector.

3. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said aerosol particles comprise particles of dry powder; and collecting or recirculating the moving gas stream in a closed system.

4. The method according to claim 3, wherein said dry powder particles are tribolelectrically charged.

5. The method according to claim 3, wherein said dry powder particles comprise carrier particles coated with a bioactive agent.

6. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said aerosol particles comprise liquid droplets; and collecting or recirculating the moving gas stream in a closed system.

7. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said aerosol particles comprise a pharmaceutical; and collecting or recirculating the moving gas stream in a closed system.

8. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said alternating electric field has a magnitude between 1 kV/cm and 30 kV/cm; and collecting or recirculating the moving gas stream in a closed system.

9. The method according to claim 8, wherein said alternating electric field has a frequency of between 1 Hz and 100 kHz.

10. The method according to claim 8, wherein said alternating field has a duty cycle different than 50%.

11. The method according to claim 10, wherein said duty cycle is 90%.

12. The method according to claim 8, wherein said alternating electric field is formed between a first electrode positioned at an end of said deposition zone opposite to and facing said dielectric substrate and a second electrode in contact with said dielectric substrate on the opposite side of where said deposit is formed.

13. The method according to claim 12, wherein said first electrode is an element of an ion emitter.

14. The method according to claim 13, wherein said aerosol particles are discharged after being deposited.

15. The method according to claim 12, wherein the contact area of said second electrode with said dielectric substrate determines the location of said deposition.

16. A method for depositing particles onto a dielectric substrate comprising the steps of:

forming an aerosol of said particles in a first region; transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein substantially all of said aerosol particles are removed from said aerosol to form said deposit; and collecting or recirculating the moving gas stream in a closed system.

17. The method according to claim 16, wherein the mass of said deposit is controlled by integrating the mass of said aerosol particles over time.

18. The method according to claim 17, where said time is determined by the measured mass of said aerosol particles.

19. The method according to claim 16, wherein multiple deposits are made using multiple deposition zones supplied from a single aerosol source by multiplexing the application of the alternating deposition field between the deposition zones.

20. A method for depositing particles onto a dielectric substrate comprising the steps of:

forming an aerosol of said particles in a first region; transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein the gas of said aerosol is selected from the group consisting of air, nitrogen, and nitrogen/carbon dioxide mixtures; and collecting or recirculating the moving gas stream in a closed system.

21. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said dielectric substrate comprises a packaging medium; and collecting or recirculating the moving gas stream in a closed system.

22. A method according to claim 21, wherein said packaging medium comprises a blister, tablet, capsule or tubule.

23. The method according to claim 22, wherein the blister comprises a plastic or metal foil blister package.

24. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric: substrate whereby charged particles are removed from the moving gas stream and deposited as oppositely charged layers on said dielectric substrate thus forming a built-up deposit, wherein said dielectric substrate comprises a pharmaceutical carrier; and collecting or recirculating the moving gas stream in a closed system.

25. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said dielectric substrate comprises a carrier for carrying said deposit from said deposition zone to a location remote from said deposition zone for further processing; and collecting or recirculating the moving gas stream in a closed system.

26. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region; and applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said dielectric substrate is edible.

27. A method for depositing particles onto a dielectric substrate comprising the steps of:

forming an aerosol of said particles in a first region;

transporting the resulting aerosol as a moving gas stream to a second region in which a deposition zone is located proximate to said dielectric substrate and applying a charge on said particles in said second region;

applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said aerosol particles are charged by an ion emitter; and collecting or recirculating the moving gas stream in a closed system.

28. The method according to claim 27, wherein said ion emitter comprises a silent electric discharge device.

29. The method according to claim 27, wherein said ion emitter comprises an ion radiation source.

30. A method for depositing particles onto a dielectric substrate comprising the steps of:

forming an aerosol of said particles in a first region;

transporting the resulting aerosol as a moving gas stream to a second region and applying a charge on said particles in said second region;

positioning said charged aerosol particles in a deposition zone located in said second region proximate to said dielectric substrate, and applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said particles comprise a solid or a liquid; and collecting or recirculating the moving gas stream in a closed system.

31. The method according to claim 30, wherein said particles comprise carrier particles coated with a bioactive agent.

32. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby charged particles are removed from the gas stream and deposited as a built-up deposit of oppositely charged layers on the surface of said dielectric substrate opposite said underlying electrode, wherein said particles comprise a pharmaceutical; and collecting or recirculating the moving gas stream in a closed system.

33. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby charged particles are removed from the gas stream and deposited as a built-up deposit of oppositely charged layers on the surface of said dielectric substrate opposite said underlying electrode, wherein said aerosol carrier is nitrogen gas; and collecting or recirculating the moving gas stream in a closed system.

34. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby charged particles are removed from the gas stream and deposited as a built-up deposit of oppositely charged layers on the surface of said substrate opposite said underlying electrode, wherein said dielectric substrate comprises a blister pack; and collecting or recirculating the moving gas stream in a closed system.

35. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby charged particles are removed from the gas stream and deposited as a built-up deposit of oppositely charged layers on the surface of said dielectric substrate opposite said underlying electrode, wherein said dielectric substrate comprises an electrically insulating material; and collecting or recirculating the moving gas stream in a closed system.

36. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby charged particles are removed from the gas stream and deposited as a built-up deposit of oppositely charged layers on the surface of said dielectric substrate opposite said underlying electrode, wherein said dielectric substrate is comprised of an electrically conducting material; and collecting or recirculating the moving gas stream in a closed system.

37. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby charged particles are removed from the gas stream and deposited as a built-up deposit of oppositely charged layers on the surface of said dielectric substrate opposite said underlying electrode, wherein said electrically charging means employs a corona wire or corona emitting points; and collecting or recirculating the moving gas stream in a closed system.

38. A method for depositing particles onto a dielectric substrate comprising the steps of:

forming an aerosol of said particles in a first region;

transporting the resulting aerosol as a moving gas stream to a second region and applying a charge on said aerosol particles in said second region;

positioning said charged aerosol particles in a deposition zone located in said second region proximate to said dielectric substrate, and applying an alternating electric field formed in said deposition zone between a first electrode positioned in said second region and a second electrode positioned underlying and in contact with said dielectric substrate whereby charged particles are removed from the moving gas stream and deposited as oppositely charged layers on said dielectric substrate thus forming a built-up deposit, wherein said step of applying an alternating electric field is performed by:

a charge source comprising a solid dielectric member, a first electrode in contact with one side of said solid dielectric member, a second electrode in contact with an opposite side of said dielectric member, with an edge surface of said second electrode disposed opposite said first electrode to define an air region at the junction of said edge surface and said solid dielectric member, and a source for applying an alternating potential between said first and second electrodes to induce ion producing electrical discharges in the air region between the dielectric member and the edge surface of said second electrode; and collecting or recirculating the moving gas stream in a closed system.

39. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby charged particles are removed from the gas stream and deposited as a built-up deposit of oppositely charged layers on the surface of said dielectric substrate opposite said underlying electrode, wherein said particles are electrically charged by triboelectric charging of said aerosol particles or induction charging of said aerosol particles; and collecting or recirculating the moving gas stream in a closed system.

40. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby particles are removed from the gas stream and deposited as a built-up deposit of oppositely charged layers on the surface of said dielectric substrate opposite said underlying electrode, wherein said aerosol particles are charged within said deposition region; and collecting or recirculating the moving gas stream in a closed system.

41. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby particles are removed from the gas stream and deposited as a built-up deposit of oppositely charged layers on the surface of said dielectric substrate opposite said underlying electrode, wherein said electrically alternating field has a magnitude between about 1 kV/cm and about 30 kV/cm; and collecting or recirculating the moving gas stream in a closed system.

42. The method according to claim 41, wherein said electrically alternating field has a frequency of oscillation between about 1 Hz and 100 kHz.

43. The method according to claim 41, wherein the duty cycle of the alternating field is adjusted to provide maximum efficiency of said particle deposition.

44. The method according to claim 41, wherein said electrically alternating field is formed between a first electrode positioned at one side of said deposition region opposite and facing said dielectric substrate and a second electrode contiguous to said dielectric substrate.

45. A method for depositing particles onto a surface of a dielectric substrate comprising the steps of:

forming an aerosol of said particles in a first region;

moving said aerosol as a moving gas steam to a second region and electrically charging said particles in said second region;

providing an alternating electric field between an electrode underlying said dielectric substrate and said aerosol particles in said second region whereby particles are removed from the gas stream and deposited as a built-up deposit of oppositely charged layers on the surface of said dielectric substrate opposite said underlying electrode, wherein the pattern of deposited material is defined by an electrically conducting mask disposed adjacent said charging means; and collecting or recirculating the moving gas stream in a closed system.

46. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby particles are removed from the gas stream and deposited as a built-up deposit of oppositely charged layers on the surface of said dielectric substrate opposite said underlying electrode, wherein the aerosol particle mass flow is monitored whereby the mass of deposited particles is controlled; and collecting or recirculating the moving gas stream in a closed system.

47. A method for depositing particles onto a surface of a dielectric substrate comprising the steps of:

forming an aerosol of said particles in a first region;

moving said aerosol as a moving gas stream to a second region and electrically charging said particles in said second region;

providing an alternating electric field between an electrode underlying said dielectric substrate and said aerosol particles in said second region whereby particles are removed from the gas stream and deposited as a built-up deposit of oppositely charged layers on the surface of said dielectric substrate opposite said underlying electrode, wherein multiple deposits are made using multiple deposition regions supplied from a single aerosol source by multiplexing the application of the alternating deposition field between the deposition regions; and collecting or recirculating the moving gas stream in a closed system.

* * * * *

UNITED STATES PATENT AND TRADEMARK OFFICE

CERTIFICATE OF CORRECTION

PATENT NO. : 6,923,979 B2
DATED : August 2, 2005
INVENTOR(S) : Fotland et al.

It is certified that error appears in the above-identified patent and that said Letters Patent is hereby corrected as shown below:

Column 10,
Line 6, "tribolelectrically" should be -- triboelectrically --.

Column 12,
Line 41, "dielectric: substrate" should be -- dielectric substrate --.

Signed and Sealed this

Thirteenth Day of June, 2006

JON W. DUDAS
*Director of the United States Patent and Trademark Office*